(12) United States Patent
Grodzki et al.

(10) Patent No.: US 11,139,082 B2
(45) Date of Patent: Oct. 5, 2021

(54) METHOD FOR CLASSIFYING A RISK FOR THROMBUS FORMATION IN AN ORGAN, SYSTEM FOR CLASSIFYING A RISK FOR THROMBUS FORMATION IN AN ORGAN, A COMPUTER PROGRAM PRODUCT AND A COMPUTER READABLE MEDIUM

(71) Applicant: Siemens Healthcare GmbH, Erlangen (DE)

(72) Inventors: David Grodzki, Erlangen (DE); Axel Heitland, Erlangen (DE); Philipp Hoelzer, Baltimore, MD (US); Rainer Kuth, Hoechstadt (DE); Sebastian Schmidt, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 98 days.

(21) Appl. No.: 16/128,912

(22) Filed: Sep. 12, 2018

(65) Prior Publication Data

US 2019/0088368 A1 Mar. 21, 2019

(30) Foreign Application Priority Data

Sep. 15, 2017 (EP) ..................................... 17191394

(51) Int. Cl.
*G06K 9/00* (2006.01)
*G16H 50/30* (2018.01)
(Continued)

(52) U.S. Cl.
CPC .............. *G16H 50/30* (2018.01); *G16H 20/00* (2018.01); *G16H 30/40* (2018.01); *G16H 50/20* (2018.01);
(Continued)

(58) Field of Classification Search
CPC . G06T 2207/20081; G06T 2207/10136; G06T 7/20; G06T 2207/30101;
(Continued)

(56) References Cited

U.S. PATENT DOCUMENTS

| 5,256,538 A * | 10/1993 | Aiken ..................... C07K 16/28 435/7.1 |
| 7,961,954 B2 * | 6/2011 | Rohaly ................ G06K 9/6215 382/209 |

(Continued)

FOREIGN PATENT DOCUMENTS

| EP | 2920722 A1 | 9/2015 |
| EP | 3084437 A1 | 10/2016 |

(Continued)

OTHER PUBLICATIONS

European Search Report 17191394.0 dated Mar. 28, 2018.

*Primary Examiner* — Alex Kok S Liew
(74) *Attorney, Agent, or Firm* — Harness, Dickey & Pierce, P.L.C.

(57) ABSTRACT

A method is for classifying a risk for thrombus formation in an organ, in particular during an atrial fibrillation. In an embodiment, the method includes providing a medical image data set via a medical imaging device; calculating a flow parameter based on the medical image data set; assigning a risk parameter based on the flow parameter calculated; and—providing the risk parameter.

18 Claims, 1 Drawing Sheet

(51) Int. Cl.
*G16H 50/20* (2018.01)
*G16H 30/40* (2018.01)
*G16H 50/70* (2018.01)
*G16H 20/00* (2018.01)
*A61B 6/00* (2006.01)
*A61B 6/03* (2006.01)

(52) U.S. Cl.
CPC .............. *G16H 50/70* (2018.01); *A61B 6/032* (2013.01); *A61B 6/486* (2013.01); *A61B 6/5217* (2013.01)

(58) Field of Classification Search
CPC ....... G06T 17/00; G06T 7/187; G06T 7/0012; G06T 7/0014; G06T 7/0016; G06T 7/174; G06T 7/62; G06T 2207/20021; G06T 7/223; G06T 19/20; G06T 2207/30048; G06T 2207/30104; G06T 2207/10081; G06T 2207/10088; G06T 2207/10104; G06T 2207/10108; G06T 2210/41; G06T 7/11; G06T 2200/04; G06T 2207/10072; G06T 2211/404; G06T 11/00; G06T 11/001; G06T 11/008; G06T 11/20; G06T 11/60; G06T 15/10; G06T 17/005; G06T 17/20; G06T 2207/10012; G16H 30/40; G16H 50/70; G16H 50/50; G16H 50/30; G16H 30/20; G16H 10/40; G16H 10/60; G16H 70/00; A61B 5/4848; A61B 6/504; A61B 5/02007; A61B 8/065; A61B 3/0025; A61B 3/14; A61B 5/7275; A61B 6/5217; A61B 6/486; A61B 5/0033; A61B 5/026; A61B 6/032; A61B 5/0263; A61B 6/481; A61B 6/507; A61B 8/5223; A61B 2576/00; A61B 5/02028; A61B 5/055; A61B 8/06; A61B 2034/104; G06F 19/321; G06F 19/00; G06K 9/6256; G06K 9/32; G06K 9/52; G06K 9/6215; G06N 3/08; A61N 5/1048; A61N 5/103; G01R 33/5608; A61M 2016/0413
USPC ........ 382/128, 129, 130, 131, 132; 600/411, 600/416, 431
See application file for complete search history.

(56) References Cited

U.S. PATENT DOCUMENTS

| | | | |
|---|---|---|---|
| 8,965,818 B2 | 2/2015 | Zillner et al. | |
| 9,349,178 B1 | 5/2016 | Itu et al. | |
| 9,538,925 B2 | 1/2017 | Sharma et al. | |
| 10,241,180 B2* | 3/2019 | Markl | A61B 5/055 |
| 2007/0041496 A1* | 2/2007 | Olivera | A61N 5/103 |
| | | | 378/65 |
| 2007/0118164 A1* | 5/2007 | Jung | A61B 90/36 |
| | | | 606/157 |
| 2007/0122017 A1* | 5/2007 | Binnig | G06K 9/6253 |
| | | | 382/128 |
| 2008/0033291 A1* | 2/2008 | Rousso | A61B 6/037 |
| | | | 600/436 |
| 2011/0181594 A1* | 7/2011 | Jung | G16H 50/50 |
| | | | 345/440 |
| 2013/0191120 A1* | 7/2013 | Zopf | G10L 19/005 |
| | | | 704/228 |
| 2013/0289364 A1* | 10/2013 | Colman | A61B 5/0836 |
| | | | 600/301 |
| 2014/0037160 A1* | 2/2014 | Matsuzaki | G06T 7/0012 |
| | | | 382/128 |
| 2014/0107935 A1* | 4/2014 | Taylor | A61B 6/5217 |
| | | | 702/19 |
| 2015/0257724 A1 | 9/2015 | Lautenschlager | |
| 2016/0004837 A1 | 1/2016 | Mittal et al. | |
| 2016/0203289 A1* | 7/2016 | Grady | G16H 50/20 |
| | | | 703/2 |
| 2016/0292372 A1 | 10/2016 | Kamen et al. | |
| 2016/0320416 A1 | 11/2016 | Pugia et al. | |
| 2016/0360958 A1* | 12/2016 | Tsuri | A61B 5/7275 |
| 2017/0046839 A1* | 2/2017 | Paik | G06K 9/00147 |
| 2017/0102390 A1 | 4/2017 | Pugia et al. | |
| 2017/0255745 A1* | 9/2017 | Mihalef | G06T 7/149 |
| 2017/0290544 A1* | 10/2017 | Yamamori | A61B 6/032 |
| 2018/0031662 A1* | 2/2018 | Markl | G06T 7/20 |
| 2018/0078146 A1* | 3/2018 | Shadforth | G16H 30/00 |

FOREIGN PATENT DOCUMENTS

| | | | | |
|---|---|---|---|---|
| WO | WO 2014127320 A1 | 8/2014 | | |
| WO | WO 2015079060 A2 | 6/2015 | | |
| WO | WO 2015184321 A2 | 12/2015 | | |
| WO | WO-2016123477 A1 * | 8/2016 | ......... | G06T 7/0016 |
| WO | WO 2016123477 A1 | 8/2016 | | |

* cited by examiner

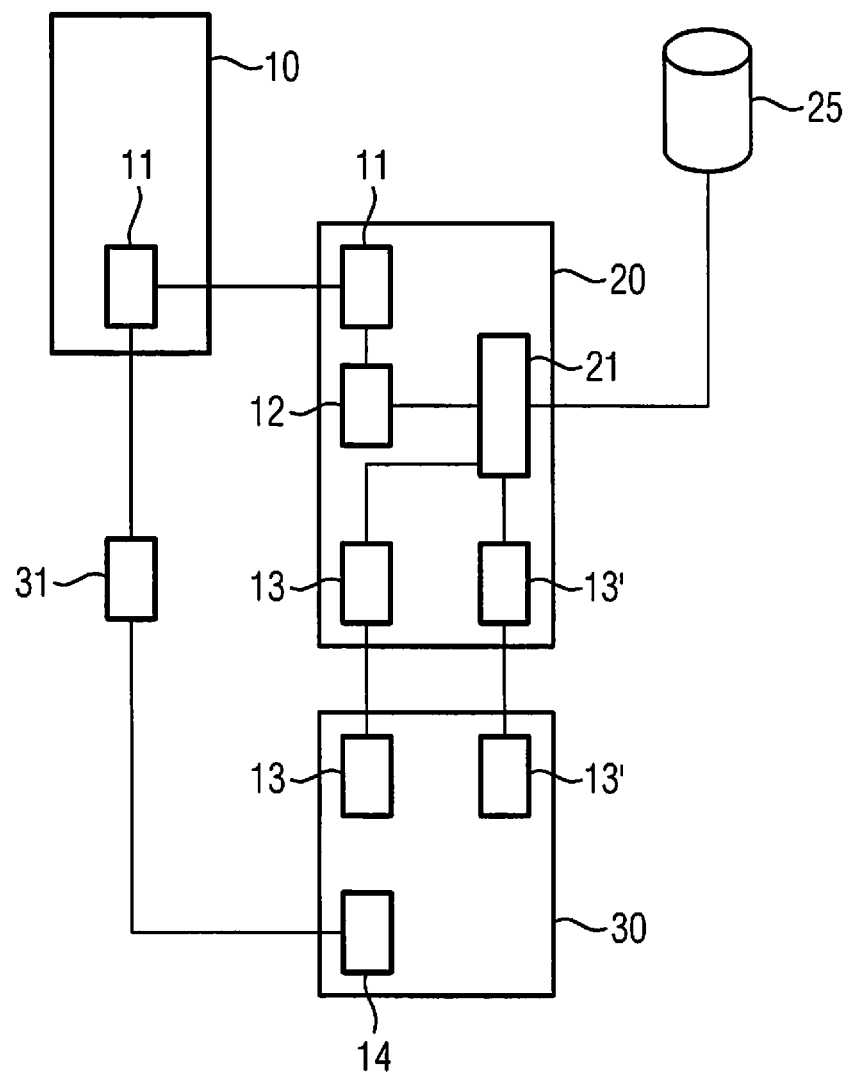

METHOD FOR CLASSIFYING A RISK FOR THROMBUS FORMATION IN AN ORGAN, SYSTEM FOR CLASSIFYING A RISK FOR THROMBUS FORMATION IN AN ORGAN, A COMPUTER PROGRAM PRODUCT AND A COMPUTER READABLE MEDIUM

PRIORITY STATEMENT

The present application hereby claims priority under 35 U.S.C. § 119 to European patent application number EP17191394.0 filed Sep. 15, 2017, the entire contents of which are hereby incorporated herein by reference.

FIELD

Embodiments of the present application generally describe a method for classifying a risk for thrombus formation in an organ, a system for classifying a risk for thrombus formation in an organ, a computer program product and a computer readable medium.

BACKGROUND

A thrombus is a blood clot that is formed inside a vein or in parts of the heart of a patient. When such a thrombus is formed, the thrombus can be carried to arteries of the patient and can cause a pulmonary embolism, a stroke or an infarct depending on its path through the arteries. Therefore, it is known from the state of the art to use medications, for example medication for suppressing blood clotting. However, these medications can cause bleedings and should be provided only to such patients having a high risk for thrombus formation. Otherwise, the medication causes more risk than the risk for a stroke or infarct without the medication. Furthermore, there is a need for rapid intervention, in particular for avoiding damages to the patients in due time.

According to U.S. Pat. No. 9,349,178 a method is suggested, wherein a hemodynamic index for location of interest in coronary arteries of a patient is determined based on receiving medical image data set of the patient and extracting patient specific coronary arterial tree geometries of the patient.

US 2015 0 257 724 deals with a method that involves capturing a contrasted data set and locating a proximal end and a distal end of a thrombosed section of a blood vessel.

SUMMARY

At least one embodiment of the present invention supports a physician or a clinician in evaluating the risk for thrombus formation, in particular in a fast and reliable way.

Embodiments of the present invention are directed to a method for classifying a risk for thrombus formation, a system, a computer program product and a computer readable computer medium.

According to a first embodiment of the present invention, a method for classifying a risk for thrombus formation in an organ, in particular during an atrial fibrillation, is provided, comprising:
 providing a medical image data set;
 calculating a flow parameter, in particular specifying the blood flow inside the organ, based on the medical image data set;
 assigning a risk parameter based on the flow parameter; and
 providing the risk parameter.

According to another embodiment of the present invention, a system comprising at least one processor, for classifying a risk for thrombus formation in an organ, in particular during an atrial fibrillation, is provided, wherein the at least one processor of the system is configured for at least:
 providing a medical image data set by a medical imaging device;
 calculating a flow parameter based on the medical image data set;
 assigning a risk parameter based on the flow parameter; and
 providing the risk parameter.

Another embodiment of the present invention is directed to a computer program product for carrying out the steps of the method according to an embodiment of the present invention when the computer program product is loaded into a memory of a programmable device.

A further embodiment of the present invention is directed to a computer-readable medium on which is stored a program elements that can be read and executed by a computer unit in order to perform steps of the method according to the present invention when the program elements are executed by the computer unit.

BRIEF DESCRIPTION OF THE DRAWINGS

In the drawings:
FIG. 1 shows a block diagram illustrating a method for classifying a risk for thrombus formation in an organ.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment of the present invention, a method for classifying a risk for thrombus formation in an organ, in particular during an atrial fibrillation, is provided, comprising:

providing a medical image data set;

calculating a flow parameter, in particular specifying the blood flow inside the organ, based on the medical image data set;

assigning a risk parameter based on the flow parameter; and providing the risk parameter.

Contrary to known methods, a risk parameter, e. g. an index of the patient's future risk for thrombus formation, can be provided to a clinician such as a physician or an operator of the medical imaging device. As a consequence, the clinician can determine a further treatment by taking into account the risk parameter.

Providing the risk parameter is based on a medical image data set, which has been recorded by using a medical imaging device such as a computer tomography (CT)-scanner, a mobile or stationary x-ray c-arm, a magnetic resonance tomography (MRT)-scanner or a ultrasound (US)-scanner. Preferably, the medical imaging device provides a two-dimensional or three-dimensional medical image data set giving information on the blood flow in the organ.

In particular, an evaluation unit is used, wherein the evaluation unit comprises a processor being configured for calculating the flow parameter of blood flow in the organ based on the medical image data set and assigning the risk parameter based on the flow parameter. In general the thrombus is formed, in particular where the blood flow is low, inside a vein or in parts of the patient, where there are eddies, e. g. in the arteria or the atrial auricle. Thus, the flow parameter allows estimating in advance the risk parameter. The evaluation unit might be incorporated into the medical imaging device or into a network such that the evaluation unit can be used by several local medical imaging devices.

It is also thinkable that the evaluation unit is configured such that at least one step of the method according to the present invention is performed at a server or a system of servers, preferably in a cloud. For using the evaluation unit it is preferably provided that the medical imaging device and the evaluation unit are in communication with each other, in particular such that at least a part of the recorded medical image data set is transferred to the evaluation unit. Preferably, the medical imaged data set is recorded by a medical imaging device. Furthermore, it is thinkable that the risk parameter is provided during or immediately after recording the medical imaged data set. Thus, the clinician is informed as soon as possible and can initiate counter measures in due time.

The term "flow parameter" preferably describes the state of the blood passing through the organ. In particular, the flow parameter is assigned or related to a specific region inside the organ, for example a specific volume in the region. Preferably, it is provided that the organ is segmented into a plurality of defined volumes or voxels, wherein to each volume or voxel a flow parameter is assigned respectively. In other words: a distribution of flow parameters is mapped to the organ. Such segmentation allows an identification of a region being relevant for the provided risk parameter. For example, regions having in general a low flow velocity can be observed in detail. Preferably, the flow parameter comprises a velocity of the blood flow, a direction of the blood flow, a mean of the velocity, a blood pressure, or the like. For example, the risk parameter is presented on a screen, such as a screen of a workstation, a tablet, a smartphone or the like. Preferably, the screen is part of the medical imaging device and the risk parameter is presented together with a visualisation of the medical imaging data set. For presenting the risk parameter on the screen, the evaluation unit is preferably in communication with the screen.

Particularly advantageous embodiments and features of the invention are given by the claims as revealed in the following description. Features of different claim categories may be combined as appropriate to give further embodiments not described herein.

According to an example embodiment of the present invention, it is provided that the medical image data set is a time-resolved medical image data set. By using the time-resolved medical image data set it is advantageously possible to extract a blood flow through the organ and to assign values of a flow parameter to the voxel. The term "time resolved medical image data set" preferably represents sequences of two-dimensional or three-dimensional images in time.

In another example embodiment, it is provided that the flow parameter is a flow velocity, wherein in particular the risk parameter is assigned to the flow velocity. Since the flow velocity is a crucial factor for the thrombus formation, the flow velocity can be interpreted as indicator for the thrombus formation. Preferably, a risk factor is assigned to a specific interval of flow velocities between an upper threshold and a lower threshold. Thus, it is possible to reduce the number of available risk parameters in order to categorize the risk parameter, for example by levels such as low risk, middle risk and high risk.

Preferably, it is provided that the flow velocity is assigned to a defined volume. As a consequence, it is avoided that the risk parameter is overrated due a statistical outlier. For example the predefined volume is greater than 2 mm3. It is also thinkable that the evaluation unit is configured such that the predefined volume is adjustable by using an input device. Thus, an operator can select a preferred predefined volume in particular a size of the predefined volume. For example, a contrast agent is injected intravenously into a patient in form of a short bolus, in particular by injecting the bolus into a crook of the arm of the patient. Subsequently, the bolus runs through vessels of the patient and consequently a differentiation between arteries and veins is possible based on measuring the relative point of time in which the bolus passes a defined location and/or measuring the flow velocity in parts of the vessels.

In particular, it is provided that the risk parameter is assigned by a trained machine learning mechanism, in particular by a deep-learning mechanism. For example, the deep learning mechanism comprises a deep convolutional neuronal network, deep Boltzmann machines, deep reinforcement learning, deep belief networks, deep recurrent neural networks, deep residual learning, support vector machines, Bayesian classifiers, k-means clustering, decision trees or inductive programs. By using machine learning mechanism it is possible to take further correlation into account for assigning the risk parameter.

For using the machine learning mechanism it is provided that the trained machine learning mechanism, e.g. a neuronal network is trained by medical imaging data sets, patient information and the formation of a thrombus in such cases. Based on this information the trained machine learning mechanism, e.g. a neuronal network establishes correlations between the medical imaging data sets and the patient information for assigning the risk parameter. Preferably, the patients are observed for a comparatively long time in order to get the information about a blood formation after recording the medical imaging data set. In particular, the result of the observation is used for training the trained machine learning mechanism, e.g. a artificial network. As a result a continuous training of the trained machine learning mechanism, e.g. a artificial network is realized. In other words: The trained machine learning mechanism, e.g. a neuronal network learns to provide the proper risk parameter in future cases.

According to another preferred embodiment, it is provided that for assigning the risk parameter a data base is used. In particular, the machine learning mechanism and/or the evaluation unit relies on the data base for assigning the risk parameter. Preferably, the data base is part of a network. As a consequence, several local medical imaging devices can rely on a common network and use a trained machine learning mechanism. Thus, the experience of the trained machine learning mechanism can grow fast.

In another embodiment, it is provided that the trained machine learning mechanism, e.g. a neural network is trained for assigning a risk parameter based on the flow parameter by at least one of the following parameters:

flow behaviour of blood in the organ, physiological parameters, such as pulse and blood pressure, laboratory parameters, such as coagulation parameters (INR, PTT, D-Dimer, thrombin time, coagulation factors) or cardiac parameters (CK, BNP or troponin)

parameters related to a viscosity of the blood, such as a number and volume of erythrocytes, a number of platelets or haemoglobin genetic risk factors, such as factor V Leiden or factor II mutation, electro-physiological parameters, such as ECK, long term ECG or specific derivations of the ECG, vessel reactivity, behaviour of a contrast agent in the organ as visible on the medical imaging data set shear forces to a vessel wall, allowing estimation of a risk for a plaque rupture, and/or anamnesis of the patient, in particular previous strokes or ischemic events.

Preferably at least some of these parameters are provided for training the trained machine learning mechanism, e.g. a neuronal network. As a consequence, besides the flow parameter, further parameters can be taken into account for assigning the risk parameter and thus for improving the reliability of providing the risk parameter. Preferably the shear forces are estimated or calculated based on the interaction or the vessel wall and the blood flow next to the vessel wall and/or a contraction movement of the vessel wall.

In another embodiment of the present invention, it is provided that a treatment suggestion is provided based on the risk parameter. Thus, a decision making process of the clinician is further supported by the method for classifying the risk parameter. Preferably, the suggested treatment is provided together with the current risk parameter.

In another example embodiment of the present invention, it is provided that a further risk parameter is provided, wherein the further parameter is assigned to a specific treatment. Thus, the operator advantageously gets an estimation of the success rate for preforming the specific treatment and thus can evaluate whether the specific treatment is promising or not. For example, the further risk parameter is smaller than the present risk parameter. Thus, the clinician is supported by knowing that the specific treatment might result in an improvement. In particular, the further risk parameter is compared to the present risk parameter and the result of the comparison is presented to the clinician. Preferably, the further risk parameter is based on a further machine learning mechanism.

Preferably, it is provided that a list of further risk parameter is provided. Thus, the clinician gets a selection of several potential treatment options to choose from. By labelling each treatment option with a corresponding further risk parameter the clinician is informed about the success rate of each treatment option and can select the one being most promising.

In particular, it is provided that the recorded medical image data set is used in the machine learning mechanism. As a consequence, each recorded medical image data set can be used for training the neuronal network. Preferably, the recorded medical image data set is transferred to the evaluation unit or the artificial network together with further information concerning the treatment.

In another embodiment of the present invention, it is preferably provided that an alert signal is emitted, when a critical value for the risk parameter is exceeded. For example, the alert signal is an acoustic of optical signal, in particular emitted from the screen or the medical imaging device. Thus, the operator of the medical imaging device is immediately informed about a risk parameter being out of range.

According to another embodiment of the present invention, a system comprising at least one processor, for classifying a risk for thrombus formation in an organ, in particular during an atrial fibrillation, is provided, wherein the at least one processor of the system is configured for at least:

providing a medical image data set by a medical imaging device;

calculating a flow parameter based on the medical image data set;

assigning a risk parameter based on the flow parameter; and providing the risk parameter.

Another embodiment of the present invention is directed to a computer program product for carrying out the steps of the method according to an embodiment of the present invention when the computer program product is loaded into a memory of a programmable device.

A further embodiment of the present invention is directed to a computer-readable medium on which is stored a program elements that can be read and executed by a computer unit in order to perform steps of the method according to the present invention when the program elements are executed by the computer unit.

In FIG. 1 a block diagram illustrating a method for classifying a risk for thrombus formation in an organ is shown. The thrombus might be formed inside a heart or a vein of a patient for example and causes such diseases as pulmonary embolism, strokes and infarcts. For such diseases there is a need for action without delay, since they causes irreparably damages to the patient within a short time period. Therefore, knowing the risk for thrombus formation is essential information for a physician to adapt the planned treatment. For classifying the risk for thrombus formation parameter providing a risk parameter 13 is suggested. Based on the risk parameter 13 the physician can determine the further treatment. As a result, a probability for thrombus formation caused by an improper treatment can be reduced.

For presenting the risk parameter 13 to a physician or an operator of an medical imaging device 10, it is provided that a medical image data set 11 of an organ, such as a heart or a vein of the patient, is recorded by the medical image device 10, such as a computer tomography (CT)-scanner, a magnetic resonance tomography (MRT)-scanner and/or an ultrasound scanner. In particular, a medical imaging data set 11 represents a time-resolved image sequence and is preferably provided to an evaluation unit 20. In particular, the medical imaging device 10 and the evaluation unit 20 are in communication with each other and at least a part of the medical image data set is transferred from the medical imaging device 10 to the evaluation unit 20.

Further, the evaluation unit 20 comprises at least one processor configured for calculating a flow parameter 12 through the organ based on the medical image data set 11, in particular the medical image data set 11 being transferred to the evaluation unit 20, and assigning a risk parameter 13 based on the flow parameter 12.

Preferably, the flow parameter 12 comprises the flow velocity, in particular a distribution of the flow velocity inside the organ, i. e. a spatial distribution of the flow velocity. As a consequence, it is possible to identify those regions having a low flow velocity below a defined threshold, for instance. These low velocities represent indicators for thrombus formation. Therefore, the risk parameter 13 is correlated to the flow velocity. By presenting the risk parameter to the physician or the operator of the medical imaging device 10, it is possible to take countermeasure for thrombus formation in due time.

In order to assign a risk parameter 13 to the flow parameter 12 it is further provided that the evaluation unit 20 has access to a data base 25, preferably via an artificial neuronal network 21. Preferably, the data base 25 is part of a server or a server system such as a cloud or a network. It is also thinkable that the evaluation unit 20 is part of the network. Furthermore, it is preferably provided that assigning the risk parameter 13 to the medical imaging data set 11 or the flow parameter set 12 is performed by the trained machine learning mechanism, e.g. a trained artificial neuronal network 21. Thus, a plurality of flow parameters 12 and additional parameters can be taken into account for determining the risk. Preferably, the trained artificial neuronal network 21 is trained by a deep learning mechanism.

Furthermore, it is provided that the risk parameter 13 is presented to the physician and/or the operator of the medical imaging device 10, in particular on a display 30 or screen of a workstation or of the medical imaging device 10. It is also thinkable that the risk parameter 13 is presented to the physician and/or the operator together with a visualization of the medical image data set 11. Preferably, for visualization of the medical image data set 11 is performed by a visualisation unit 31 providing a visualized data set 14 to the display 30. In particular, a critical region being relevant for the assigned risk parameter is highlighted in the visualized data set 14 based on the risk parameter. Preferably, an alert signal is provided, when the risk parameter 13 exceeds a critical threshold. It is also conceivable that a further risk parameter 13' is provided, wherein the further risk parameter 13' is assigned to a potential treatment. Thus, the physician is informed about the chances for reducing the risk for thrombus formation by using a specific treatment.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a risk parameter for future thrombus formation in an organ of a patient, comprising:
   providing a medical image data set of the organ;
   calculating a flow parameter of blood passing through an organ based on the medical image data set, wherein the flow parameter is a flow velocity and the flow velocity is assigned to a defined volume;
   assigning a risk parameter for future risk of thrombus formation based on the flow parameter calculated, wherein the risk parameter is related to the flow velocity; and providing the risk parameter for future risk of thrombus formation, wherein a processor is configured such that the defined volume is adjustable using an input device, wherein a treatment suggesting is provided based on the risk parameter, wherein a further risk parameter for future thrombus formation is provided, and wherein the further risk parameter is assigned to a specific suggested treatment.

2. The method of claim 1, wherein the medical image data set is a time-resolved medical image data set.

3. The method of claim 1, wherein the assigning of the risk parameter includes assigning the risk parameter via a trained machine learning mechanism that accesses a data base comprising previous calculated risk parameters of a plurality of different patients and assigns the risk parameter based on an assessment of the previous calculated risk parameters stored in the data base.

4. The method of claim 1, wherein the assigning of the risk parameter includes accessing a data base comprising previous calculated risk parameters of a plurality of different patients.

5. The method of claim 1, wherein the assigning of the risk parameter includes assigning the risk parameter via a neural network, trained for assigning the risk parameter based on the flow parameter by at least one of:
 flow behaviour of blood in the organ,
 at least one physiological parameter,
 at least one laboratory parameter,
 at least one parameter relating to a viscosity of the blood,
 at least one genetic risk factor,
 at least one electro-physiological parameter,
 vessel reactivity,
 behaviour of a contrast agent in the organ,
 shear forces to a vessel wall allowing estimation of a risk for a plaque rupture, and
 anamnesis of the patient.

6. The method of claim 1, wherein a list of further risk parameters is provided.

7. The method of claim 3, wherein the medical image data set provided is used in the machine learning mechanism.

8. The method of claim 1, further comprising:
 emitting an alert signal upon a critical value for the risk parameter being exceeded.

9. A system for providing a risk for future thrombus formation in an organ of a patient, the system comprising:
 a medical image device to provide a medical image data set of the organ; and at least one processor configured to at least
 calculate a flow parameter of blood passing through an organ based on the medical image data set,
 assign a risk parameter for future risk of thrombus formation based on the flow parameter calculated; and
 a display to display the risk parameter for the future risk of thrombus formation, wherein a treatment suggestion is provided based on the risk parameter, wherein a further risk parameter for future thrombus formation is provided, and wherein the further risk parameter is assigned to a specific suggested treatment.

10. A non-transitory computer-readable product storing program segments, readable and executable by at least one processor to perform the method of claim 1 when the program segments are executed by the at least one processor.

11. A non-transitory computer-readable medium storing program elements, readable and executable by a computer unit to perform the method of claim 1 when the program elements are executed by the computer unit.

12. The method of claim 3, wherein the trained machine learning mechanism is a trained deep-learning mechanism.

13. The method of claim 2, wherein the assigning of the risk parameter includes assigning the risk parameter via a neural network, trained for assigning the risk parameter based on the flow parameter by at least one of:
 flow behaviour of blood in the organ,
 at least one physiological parameter,
 at least one laboratory parameter,
 at least one parameter relating to a viscosity of the blood,
 at least one genetic risk factor,
 at least one electro-physiological parameter,
 vessel reactivity,
 behaviour of a contrast agent in the organ,
 shear forces to a vessel wall allowing estimation of a risk for a plaque rupture, and
 anamnesis of the patient.

14. The system of claim 9, wherein the system is for providing a risk for future thrombus formation in an organ of a patient during an atrial fibrillation.

15. The system of claim 9, wherein the at least one processor is further configured to determine a treatment suggestion, based on the risk parameter provided, and wherein the display is further configured to display the treatment suggestion determined.

16. A system for providing a risk for thrombus formation in an organ of a patient, the system comprising:
 at least one processor configured to at least
 calculate a flow parameter of blood passing through an organ based on a medical image data set of the patient;
 assign a risk parameter for future risk of thrombus formation based on the flow parameter calculated; and
 provide the risk parameter for the future risk of thrombus formation, wherein a treatment suggestion is provided based on the risk parameter, wherein a further risk parameter for future thrombus formation is provided, and wherein the further risk parameter is assigned to a specific suggested treatment.

17. The system of claim 16, wherein the at least one processor is further configured to provide a treatment suggestion, based on the risk parameter provided.

18. The method of claim 1, wherein the risk parameter is an index of the patient's future risk for thrombus formation.

* * * * *